United States Patent [19]

Duchane

[11] 4,376,751

[45] Mar. 15, 1983

[54] PRODUCTION OF SUPER-SMOOTH ARTICLES

[75] Inventor: David V. Duchane, Los Alamos, N. Mex.

[73] Assignee: The United States of America as represented by the Department of Energy, Washington, D.C.

[21] Appl. No.: 268,425

[22] Filed: May 29, 1981

[51] Int. Cl.³ .............................................. B29C 25/00
[52] U.S. Cl. ..................................... 264/341; 428/409
[58] Field of Search .......................... 264/341; 428/409

[56] References Cited

U.S. PATENT DOCUMENTS

| | | | |
|---|---|---|---|
| 2,209,940 | 7/1940 | Smith | 264/341 |
| 2,572,719 | 10/1951 | Ginell et al. | 264/341 |
| 3,625,755 | 12/1971 | Potrafke | 117/160 |
| 3,684,553 | 8/1972 | Van Dyk | 264/341 |
| 4,133,912 | 1/1979 | Stuart | 264/341 |
| 4,302,418 | 11/1981 | Cullis | 264/341 |

OTHER PUBLICATIONS

Chemical Abstracts, vol. 82, 1975, pp. 43-44, No. 98967m.
Chemical Abstracts, vol. 83, 1975, p. 83, No. 115655y.
Chemical Abstracts, vol. 90, 1979, p. 53, No. 90: 169698c.
Chemical Abstracts, vol. 84, 1976, p. 50, No. 84: 606589.
Daniels et al. Physical Chemistry, 2nd Edition, Wiley and Sons, New York, 1963, p. 354.
Modern Plastics Encyclopedia, pp. 533-536, Gross Editor—in—Chief (McGraw—Hill, NY 1974-1975).

*Primary Examiner*—James H. Derrington
*Attorney, Agent, or Firm*—Elizabeth O. Slade; Paul D. Gaetjens; Richard G. Besha

[57] ABSTRACT

Super-smooth rounded or formed articles made of thermoplastic materials including various poly(methyl methacrylate) or acrylonitrile-butadiene-styrene copolymers are produced by immersing the articles into a bath, the composition of which is slowly changed with time. The starting composition of the bath is made up of at least one solvent for the polymer and a diluent made up of at least one nonsolvent for the polymer and optional materials which are soluble in the bath. The resulting extremely smooth articles are useful as mandrels for laser fusion and should be useful for a wide variety of other purposes, for example lenses.

12 Claims, 6 Drawing Figures

PRODUCTION OF SUPER-SMOOTH ARTICLES

BACKGROUND OF THE INVENTION

This invention relates generally to a method of producing super-smooth articles made of thermoplastic materials and to the articles thus produced and relates more particularly to a method of producing super-smooth articles made of acrylic polymers or acrylonitrile-butadiene-styrene polymers. The invention is a result of a contract with the Department of Energy (Contract No. W-7405-ENG-36).

In the following, thermoplastic materials are defined to include linear and branched organic molecular structures that will repeatedly soften when heated and harden when cooled.

In the production of inertial confinement fusion (ICF) targets, mandrels with super-smooth surfaces are extremely important to the fabrication of metal confinement shells having the required degree of uniformity. To date, mandrels have been made almost exclusively from glass or metallic materials because it has not been considered practical to obtain plastic mandrels with the required degrees of surface smoothness and/or thermal stability. Metal is deposited onto the mandrel by a variety of techniques; and, any nonuniformity on the mandrel will appear on the target. Then, the mandrel is dissolved out, leaving a hollow metal confinement shell target. Using glass or metal presents severe difficulties when the mandrel is to be removed from the shell, however, since these materials tend to be soluble only in liquids which are difficult to handle (e.g., hydrofluoric acid) or which also attack the shell itself.

Although very smooth flat surfaces of some amorphous materials can be produced by pouring the amorphous material when it is a fluid, the smoothest rounded or formed (as opposed to flat) surfaces of plastics with softening points too low to permit the type of polishing used for glassy materials which have been obtained in the prior art are mechanically machined surfaces obtained by using a diamond knife. However, producing such a surface is very expensive, the surfaces invariably have machining ridges (which can be viewed at 1600X) left by the tooling; and in order to produce small articles by such a method, special equipment would be required for holding the articles while they are being machined. Furthermore, it is difficult to produce super-smooth surface finishes on polymers by mechanical means because heat produced by frictional processes is dissipated much more slowly by plastics than by metals or glass, and the lower softening points of these materials often result in gumming and poor finish control, as disclosed in *Modern Plastics Encyclopedia*, pp. 533-536, S. Gross, Editor-in-Chief (McGraw-Hill, NY, 1974).

In the past, solvent treatments of polymer surfaces have often involved the use of agents designed to make the polymer more receptive to inks and dyes, to increase the chemical reactivity of the polymer at its surface, or to impart other specialized properties to the material. These treatments generally involved the creation of a surface which was microscopically roughened, rather than smoothed.

In several Russian papers referenced in *Chemical Abstracts*, surface smoothing by solvent treatment was disclosed. The references include (1) V. L. Avramenko et al., "Improving the Strength Properties of Polymers by Removing Surface Defects," Fiz. Khim. Polim. Kompozitsii, 143-150 (1974) (Russ.), (2) A. A. Shturman et al., "Strengthening of Plastic Products in a Medium of Solvents for Polymers," Fiz.-Kihm. Mekh. Mater., 11(2), 78-83 (1975) (Russ.), and (3) A. A. Shturman et al., "Stabilization of Poly(Methyl Methacrylate)," Otkrytiya Izobret., Prom. Obraztsy, Tovarny Znaki (6), 86 (1979). In these references, an acrylic polymer (AST-T or poly(methyl methacrylate)) was subjected to a treatment at an elevated temperature of 80°-85° for 3-4 minutes. In reference (1), the acrylic polymer was immersed into amyl alcohol and butyl acetate; in reference (2), into amyl alcohol or butyl (or ethyl, methyl, propyl or isobutyl) acetate; and in reference (3), into a "stabilizer solution." The strength of the material improved and the surface was smoothed to some extent, although microscopic smoothing was not mentioned. It is believed that the surface under a magnification of about 20-40X would take on a wrinkled appearance as was observed in Example 1, described below.

In a fourth Russian reference listed in *Chemical Abstracts*, A. A. Shturman et al., "Surface Treatment by Solvents as a Method for Modification of the Properties of Polymeric Articles," Tezisy Dokl.—Resp. Konf. Vysokomol. Soedin., 3rd, 112-113 (1973) (Russ.), (the authors being two of the authors listed in the Russian references 1-3 above), the surfaces of molded plastic articles made of an acrylic polymer or acrylic resin were smoothed at an unspecified temperature by treatment with amyl alcohol or an acetate (methyl, ethyl, propyl, butyl, or isobutyl). Again, however, it is believed that the surface would most probably have taken on a wrinkled appearance (as in Example 1 below) and that no super-smooth surface would be achieved.

In U.S. Pat. No. 3,625,755 to Potrafke, coating with or impregnation by a metal-forming complex is disclosed. However, the process is not a smoothing process and where impregnation is carried out the material is impregnated throughout the entire structure, not just near the surface; and thus the method and articles produced are different from those of the present invention.

Some smoothing is obtained when one uses varnish remover, for example, to smooth scratches and surface imperfections. However, such smoothing does not produce a microscopically smooth surface which is necessary for producing laser fusion targets and which is desirable for other articles, for example lenses.

Therefore, despite what has been known in the prior art, a need has existed until now for a method of producing super-smooth rounded or formed surfaces made of thermoplastic material which are smoother than those obtained by diamond knife machining. By the term "super-smooth" is meant surface quality wherein all defects are smaller than about 4 $(\mu m)^2$ in area.

SUMMARY OF THE INVENTION

An object of this invention is a method for producing super-smooth articles of manufacture made of certain thermoplastic materials and having rounded or formed surfaces.

Another object of this invention is a method of producing super-smooth articles made of poly(methyl methacrylate) or acrylonitrile-butadiene-styrene polymers.

A still further object of this invention is a super-smooth article of manufacture made of thermoplastic material and having rounded or formed surfaces.

Another object of this invention is a super-smooth mandrel made of poly(methyl methacrylate).

A further object of this invention is a super-smooth lens made of acrylic, the light transmission of the lens being enhanced by the absence of surface defects.

Yet another object of this invention is a super-smooth acrylic optical fiber having special properties.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, a method of producing at least one super-smooth surface on an article made of thermoplastic material which can be poly(methyl methacrylate) or an acrylonitrile-butadiene-styrene polymer or equivalents thereof comprises: (a) immersing at least a portion of the article into a bath consisting essentially of (1) at least one solvent for the thermoplastic material, (2) at least one nonsolvent for the thermoplastic material, and (3) optional accessory material which is soluble in the bath and which one may wish to deposit into the thermoplastic material; and (b) slowly removing the solvent from the bath by diluting the bath with the nonsolvent and the optional accessory material (both of which make up the diluent), the nonsolvent being a mixture of water and a water-soluble polymer having a molecular weight within the range from about 2000 to about 20,000, the solvent being selected from the group consisting of ketones and esters which show some significant mutual solubility with water, and the rate of dilution of the bath being such that it results in extraction of the solvent from the thermoplastic material on a molecular scale, rather than on a massive scale.

In an especially preferred embodiment, the thermoplastic material is acrylic (i.e., poly(methyl methacrylate)), the solvent is acetone, and the nonsolvent is a particular mixture of water and a polyethylene glycol having a particular molecular weight. Using this combination, extremely smooth rounded or formed surfaces were obtained which had very few imperfections and no visible machining marks when viewed at a magnification of up to 1600× (unlike the smoothest prior art rounded or formed surfaces of thermoplastic material, which were obtained by diamond knife machining).

It is believed that such super-smooth rounded or formed acrylic and acrylonitrile-butadiene-styrene copolymer surfaces have never before been obtained.

In the method of the invention, no elevated temperature need be used and thus bulk deformation of articles being smoothed is not a problem.

An unexpected result was observed upon using the method of the invention. When $CuBr_2$ was dissolved in the diluent (as described below in Example 6), the colored solution of $CuBr_2$ chemically infused into an acrylic rod so as to produce a uniformly dark annulus surrounding an inner region which appeared to have no infused $CuBr_2$. A sharp boundary between the two regions was observed. The uniformity and the sharp cutoff could not have been expected based upon classical concepts of fluid diffusion (as described for example in Daniels and Alberty, *Physical Chemistry*, 2nd Edition (Wiley and Sons, New York, 1963) p. 354). Therefore, it is believed that besides being useful for obtaining extremely smooth surfaces, the method of the invention can be used to implant simply, efficiently, and to a controlled depth a variety of substances into the thermoplastic material of which the surface is being smoothed. The infused material cannot be scratched off easily, as coatings can. Some applications of this implantation include the following. A catalyst can be deposited into the surface of the thermoplastic material and held in that position. This could be very useful if a foamed plastic having a very large surface area is the catalyst support and the catalyst is chemically infused by the method of the invention into the support. Another application of the smoothing method of the invention is to infuse an integral protective barrier into the smoothed surface of a thermoplastic material. Another application of the method is to produce an acrylic optical fiber into which a material is infused, producing two layers having different refractive indexes and having a very sharp boundary between the layers. Another application of the method of the invention is to infuse lead ions into an amorphous material, thus producing a radiation barrier on the amorphous material. Yet another application of this invention is to decorate thermoplastic materials.

The method of the invention can also be used to infuse volatile materials into the surface of a thermoplastic material. It has been noted that when acrylic was the thermoplastic material and when water was the infused material, the water was released very slowly from the acrylic. This release suggests, therefore, applications of the method of the invention for timed-release biological implants, for waste control and various industrial processes which would make use of such a release of an infused volatile compound in the thermoplastic material, for room deodorants, and for long-term bacteriocidal or pH control.

The applications described above make use of the method of the invention which (1) can produce an extremely smooth surface, (2) can allow implantation of a secondary substance into a polymer to a well-defined depth (thus allowing a modified surface layer to be built around a structurally sound core), and (3) allows infusing volatile materials into a thermoplastic material, from which the volatile materials will escape over periods of weeks to months.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings are shown scanning electron micrographs (SEM's) which illustrate improvements in surface quality which result from using the method of the invention.

DESCRIPTION OF THE PREFERRED EMBODIMENTS

In the practice of the method of the invention, the uniformity of the surface of a thermoplastic material is greatly improved by placing the material into a bath, through which a mixture (which varies with time) of materials is circulated over an extended period of time. The thermoplastic material should be a material which is capable of being softened and being penetrated by components of the bath without being dissolved in the bath.

The bath consists essentially of at least one solvent and at least one nonsolvent for the thermoplastic material, together with optional accessory material which is soluble in the bath and which one may wish to deposit into the amorphous material. It is believed that the use of the nonsolvent is critical to achieving the supersmooth surfaces; and this is demonstrated below in Examples 1 and 3.

The solvent should be at least one material selected from the group consisting of ketones and esters which show some significant mutual solubility with water, that group including acetone, methylethyl ketone, diethylketone, ethyl acetate, methyl acetate, isopropyl acetate, and methyl propionate.

The requirements of the initial solvent and nonsolvent system are (1) the solvent(s) and the nonsolvent(s) should be (or should be capable of being made) compatible with one another (i.e., so that they form a homogeneous solution) and (2) the system should be capable of softening and swelling, but not dissolving the polymer. If a smooth surface is to be obtained, the nature of the nonsolvent component must be such that it does not separate out into significant agglomerations, bubbles, or the like, either within the polymer matrix or at the surface of the polymer, as the treatment proceeds. The tendency for this separation to occur appears to be a function of the mobility of the nonsolvent and its inherent compatibility with the polymer material.

Figure 4:
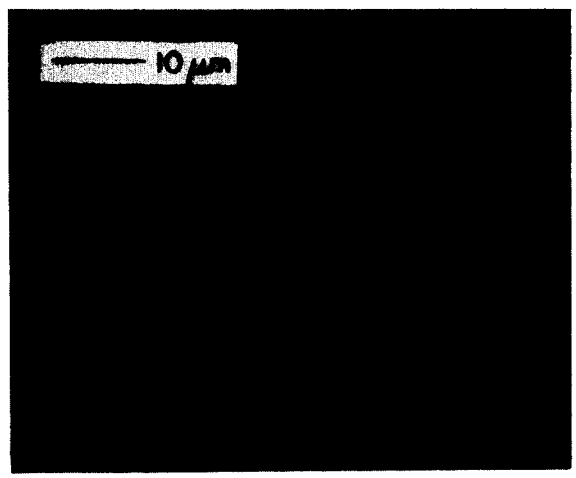
In FIG. 4, at a magnification of 1600× is shown a rounded poly(methyl methacrylate) surface which was obtained by the method of the invention, as described below. No machining marks are present, and significantly fewer and smaller surface imperfections exist than in FIG. 2. Here, the solvent was acetone and the nonsolvent was a mixture (described below) of water and polyethylene glycol.

Examples of suitable systems include but are not limited to the following. Poly(methyl methacrylate) (i.e., acrylic) can be very effectively smoothed even at a microscopic level (as shown in FIG. 4 and described in Example 5) by placing the acrylic into a bath having acetone as the solvent material and having a mixture (as the nonsolvent component, which is used as the diluent) of polyethylene glycol (i.e., PEG) and water. Alternatively, another suitable system for improving the uniformity of a surface of acrylic is to use acetone as the solvent but to use as the diluent a mixture of water, polyvinylpyrrolidone, and a small amount of isopropyl alcohol (which improves the compatibility of water and acrylic). In this system, the resulting acrylic surface has a spongy-like appearance and is very smooth and uniform. (See FIGS. 5 and 6 and Example 7).

For other thermoplastic materials, the starting solution must consist of a bath consisting of a solvent (e.g., acetone for polystyrene and polycarbonate; cyclohexane for polymethylpentene) and a nonsolvent. The nonsolvent can consist of several components but as a whole it must be compatible enough with the polymer that it does not separate or agglomerate into occlusions greater than micron sized dimensions as the reaction proceeds. The nonsolvent should thus have polarity character somewhat similar to the polymer it is used with. A polymer with no strongly polar sites would require a nonsolvent component which also is generally nonpolar in nature. The solvent for the polymer must, of course, by nature of the solution process, have polarity characteristics similar to the polymer. For example, for a polymer such as poly(methyl methacrylate) a combination of water and PEG is a suitable nonsolvent component; however, a polymer like polymethylpentene which does not have highly polar sites may require a nonsolvent component consisting of an organic liquid such as acetone in combination with a fatty acid ester or wax such as beeswax.

Additives can be added to the starting solution of solvent and nonsolvent bath, provided that the additive(s) dissolve(s) in the starting solution. See Example 6 below. Examples of suitable additives which must be reasonably soluble in both the starting solution and end solution are metal salts (e.g., $CuBr_2$, $CuCl_2$, $Pb(NO_3)_2$; catalysts (e.g., $PdCl_2$, $AlCl_3$, and $FeCl_3$); volatile materials (e.g., calcium hypochlorite, iodine, and essential oils (e.g., oil of wintergreen, anise, and peppermint)); and organic materials (e.g., neutral red, phenol red, and nickel acetoacetate).

The total volume of starting solution is important only in that it should be sufficient to immerse the portion of the thermoplastic material which is to be smoothed by the method of the invention. However, the rate of dilution of the solvent (described below) is important and is related to the total bath volume. For example, if the total volume is reduced, the absolute rate of dilution must be reduced.

The starting ratio (by volume) of solvent to diluent should be generally selected so that attack on the amorphous material results, the attack being sufficient to soften but not dissolve the amorphous material. When the amorphous material is acrylic, when the solvent is acetone, and when the nonsolvent is a mixture of water and polyethylene glycol (PEG), the ratio of solvent-:diluent (by volume) will generally be within the range from about 40:60 to about 80:20 and more preferably will be within the range from about 60:40 to about 80:20. This same general range is expected to be effective when the plastic treated is acrylonitrile-butadiene-styrene. (See Example 8, below.) The PEG should have a molecular weight within the range from about 2000 to about 15,000 for best smoothing. A more preferred range is about 3000 to about 6000 because low molecular weight varieties tend to form microscopic blotches on the treated surface and high molecular weight varieties lead to more rapid increases in viscosity of the nonsolvent (and thus a lower maximum pumpable concentration of the PEG). Best results were obtained for PEG-4000 (having an approximate molecular weight of 4000). Additionally, surface smoothing appears to improve as the amount of PEG relative to the amount of water is increased. The amount of PEG which can be incorporated in the nonsolvent is limited by the viscosity of the mixture because eventually a point is reached at which the solution is too thick to pump. Therefore, the weight ratio of water:PEG in the mixture of water and PEG should be within the range from about 75:25 to about 40:60 (by weight) for the molecular weight range described above and often will be about 50:50 (by weight) for the preferred PEG-4000.

When the amorphous material is acrylic, when the solvent is acetone, and when the diluent is a mixture of water, polyvinylpyrrolidone, and a small amount of isopropyl alcohol (less than about ½%), the starting volume ratio of solvent:diluent will generally be within the range from about 25:75 to about 65:35; and when the weight ratio of polyvinylpyrrolidone:water is about 50:50, the optimum starting volume ratio of acetone:diluent has been found to be about 50:50.

The final concentration of solvent:diluent at the end of the smoothing process should be essentially pure nonsolvent.

The length of time during which the article remains in the starting bath (before any additional diluent is added) should generally be as short as possible. Generally, it is desirable to have the method of the invention produce super-smooth surfaces in a minimum amount of time; and, therefore, the starting ratio of solvent:diluent and the rate of dilution will both be chosen to be relatively large and the dilution will be started as soon as possible after insertion of the article into the bath.

The rate of dilution will be limited to that which will result in extraction of the solvent from the polymer matrix on a molecular scale rather than on a massive scale.

The temperature of the bath can be elevated if desired but for convenience can be maintained at room temperature.

The flow rate through the bath must be slow enough to prevent shearing of the surface being smoothed.

The length of time during which diluent is added to the bath (i.e., approximately the total time of the object in the bath) is important to the degree of penetration of additives into the amorphous material and may be important to smoothing. It should generally be less than 24 hours (for convenience) and preferably will be 16–20 hours.

If small rounded or formed objects are to be smoothed, the bath can be in the shape of an upright funnel with the fluid inlet at the bottom of the funnel and fluid outlet(s) near the top. This would allow the objects to remain suspended in the bath in spite of changes in fluid density.

EXAMPLES

Figure 1:
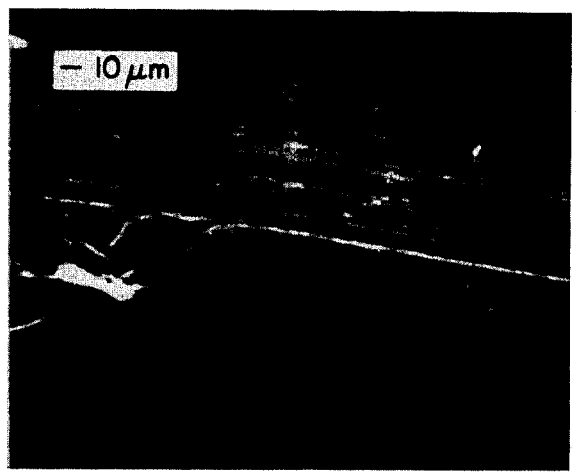
In FIG. 1, the surface of an untreated commercially available poly(methyl methacrylate) rod is shown at a magnification of 300×.

The following examples illustrating various embodiments of the invention were carried out. In examples 1–7, the starting materials were cylindrical acrylic (poly(methyl methacrylate)) rods. In FIG. 1 is shown the untreated surface of one of these commercially available acrylic rods. In example 8, a cylindrical rod made of acrylonitrile-butadiene-styrene polymer obtained by injection molding and subsequent machining of resin from Borg-Warner Corporation and having the tradename Cycolac was used. In Example 9, a square-shaped acrylic rod was used.

EXAMPLE 1 (CONTROL)

An acrylic rod was immersed in pure acetone for 5 minutes, then removed, and allowed to dry. Immediately after removel from the acetone, the surface of the rod appeared to be smooth. However, the surface became microscopically undulating as the acetone evaporated. Microscopic examination at about 20–40× showed that surface scratches had been eliminated but that transverse ripples, rounded pits, and lumps were now present.

From the results in Example 1 and Example 3 (below), it appears that a nonsolvent is necessary to achieve a super-smooth surface. The nonsolvent allows the controlled extraction of the solvent from the substrate.

EXAMPLE 2 (CONTROL)

An acrylic rod was immersed in a stationary mixture of 75 v/o acetone and 25 v/o water for 15 minutes, then removed, and allowed to dry. The degree of surface rippling was greatly reduced as compared with Example 1, but imperfections which appeared to be due to water-spotting were scattered across the surface. The imperfections were in the form of irregular shaped indentations in the surface. Comparing the results in Example 2, Example 4 and Example 5 (below), one can observe that the proper choice of solvent-nonsolvent system is critical to achieving super-smooth surfaces.

EXAMPLE 3 (CONTROL)

An acrylic rod was exposed to vapor from boiling acetone for about 5 minutes. The vapor temperature was approximately 57° C. Upon removal from the treatment chamber, the surface was clear and superficially smooth at first, but the surface gradually took on a blistered appearance as white, circular imperfections began to form on it.

EXAMPLE 4

Figure 3:
In FIG. 3 is shown a surface of poly(methyl methacrylate) obtained by using acetone as the solvent and only water as the nonsolvent, at a magnification of 300×. The surface appears to be undulating with numerous pits.

An acrylic rod ⅛ inch in diameter was immersed to a depth of about 8 inches in one arm of a U-tube containing a mixture of 75 v/o acetone and 25 v/o water, with a total volume of about 125 ml. The fluid was kept continuously circulating through the U-tube and past the acrylic rod at a rate of about 10 ml/minute by means of a circulating pump attached to the U-tube with flexible tubing. Dilution of the mixture with water was begun immediately after placing the tube in the bath. This was accomplished by placing a "T" in the circulating loop at a point just above the entry of the fluid into one arm of the U-tube and pumping diluent into the system with a peristaltic metering pump at a rate of about 0.4 ml/min. Circulation of the fluid served to promote rapid and uniform mixing of the diluent into the bath. An overflow tube, located on the arm of the U-tube opposite the diluent inlet, provided a means for maintaining constant bath volume. Using the conditions described here, the composition of the treatment bath was gradually changed from 75 v/o acetone:25 v/o water to about 99.5 v/o water over a period of about 20 hours. After approximately 20 hours in the treatment bath, the rod was removed, washed with water, allowed to dry, and subsequently examined. Under an optical microscope at 20-40×, the surface was found to be mottled with many small bubbles on or beneath the surface. Scanning electron microscopy (SEM) at 300× showed an undulating surface with numerous pits, as shown in FIG. 3.

EXAMPLE 5 (INVENTION)

Figure 2:
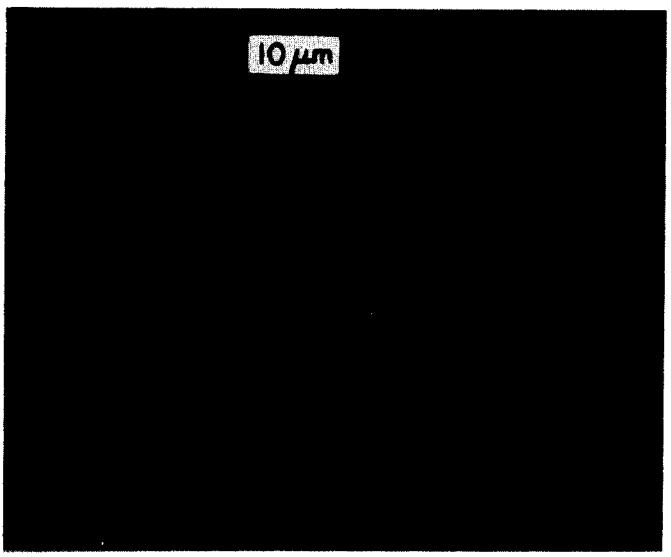
In FIG. 2 is shown the surface of the same type of material that was shown in FIG. 1 after it had been subjected to diamond knife machining, this surface representing the best known prior art surface quality on a rounded or formed article made of thermoplastic material at a magnification of 1600×. The channels shown in the SEM are the machining marks. The length of the long line represents a distance of about 10 μm.

The experiment described in Example 4 was repeated with the sole exception that where water had been used in the previous example, a mixture of 50 w/o water and 50 w/o polyethylene glycol-4000 (with a molecular weight of about 4000) was now used. Examination of the sample after treatment under an optical microscope at 140× showed a smooth, essentially defect-free surface. SEM's (one of which is shown in FIG. 4) at 1600×, likewise, showed a smooth surface with a complete absence of the undulations and pits found for the sample of Example 4. The area of the largest defect was about 4 $(\mu m)^2$ and the total number of all other defects (none of which had an area greater than 1 $(\mu m)^2$) in FIG. 4 is less than about 50 per 3000 $(\mu m)^2$. In FIG. 2, on the other hand, the area of the largest defect was about 16 $(\mu m)^2$ and the total number of defects (not even including machine marks) was greater than 70 per 3000 $(\mu m)^2$. It is believed that at least some of the defects in FIG. 4 are probably due to contamination from the atmosphere because the treated sample was left unprotected for several months. Additionally, the surface had no blotches. The surface shown in FIG. 4 is the smoothest surface which has been obtained with the bath system made of acetone, PEG, and water.

In a series of further runs, various other grades of PEG were used in conjunction with water as diluent materials. When the diluent was composed of 90 w/o water and 10 w/o PEG-1000, the undulatory surface features were somewhat reduced from those shown in FIG. 3. At 50 w/o water and 50 w/o PEG-1000, the undulations essentially disappeared but blotchy regions were scattered across the surface of the rod. Using a diluent of 50 w/o water and 50 w/o PEG-1540, the surface blotches were noticeably smaller but still numerous. Experiments conducted using low molecular weight (600) PEG and very high molecular weight (20,000) PEG additives gave totally unsatisfactory results. At both of these extremes, the modified surfaces had wrinkles which were apparent to the unaided eye.

EXAMPLE 6 (INVENTION)

The experiment of Example 5 was repeated once again, but now using a combination of three parts by weight of water, three parts by weight of PEG-4000, and two parts by weight of $CuBr_2$ in place of the water used in Example 4. In this case, SEM photographs showed the surface of the rod to have generally a smoothness (as regards maximum defect size) as good as that of Example 5 above (although more defects were here present than in Example 5), but several other interesting observations were also made. A section taken from the rod revealed that the diluent, which in this example was colored a deep green, had penetrated about 1300 $\mu m$ into the core of the rod (about 72% of the distance to its center), and that the limit of penetration was marked, not by a gradual diminution of the intensity of the colored species, but rather by a sharp interface which clearly separated the infused sector from the unaffected core of the material. The interface appeared to be sharp even when viewed at a magnification of 140×.

Weight measurements were made to determine the amount of material infused into the rods of examples 4, 5, and 6, described above. The following results were obtained:

TABLE 1

| Rod from Example | Time after Removal from Treatment Bath (hr.) | Weight/Weight Prior to Treatment |
| --- | --- | --- |
| 4 | 0.3 | 1.059 |
|   | 1.5 | 1.044 |
|   | 26 | 1.033 |
|   | 1080 | 1.023 |
| 5 | 0.3 | 1.101 |
|   | 1.3 | 1.096 |
|   | 19 | 1.082 |
|   | 1080 | 1.052 |
| 6 | 0.5 | 1.143 |
|   | 2.3 | 1.133 |

EXAMPLE 7

In this example, the same basic procedure as described above in Example 4 was used. However, here polyvinylpyrrolidone (molecular weight 10,000) in water was used as the diluent. However, when these two materials were mixed, a flocky precipitate appeared. This was eliminated by adding drop-wise a small amount (less than ½ w/o) of isopropyl alcohol.

Figure 5:
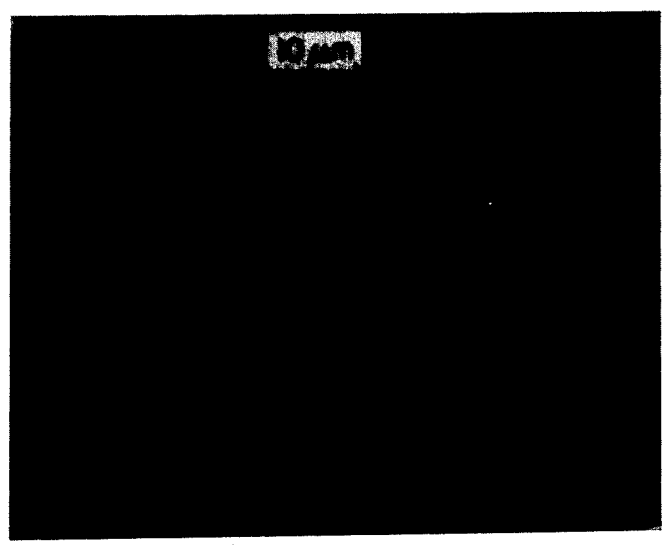
In FIG. 5 is shown another surface at 1600× of poly(methyl methacrylate) obtained by using the method of the invention. Here, the solvent was acetone and the nonsolvent was a mixture (described below) of polyvinylpyrrolidone, water, and isopropyl alcohol. This surface has very few imperfections and has a spongy-like appearance.

In example 7a, the results of which are shown in FIG. 5, the starting composition of the bath was 60 v/o acetone and 40 v/o diluent. The diluent was made up of 40 w/o polyvinylpyrrolidone-10,000, 60 w/o water and less than ½ w/o isopropyl alcohol. As can be seen in FIG. 5, the resulting surface is very uniform and smooth and has very few imperfections, even when viewed at a magnification of 1600×.

Figure 6:
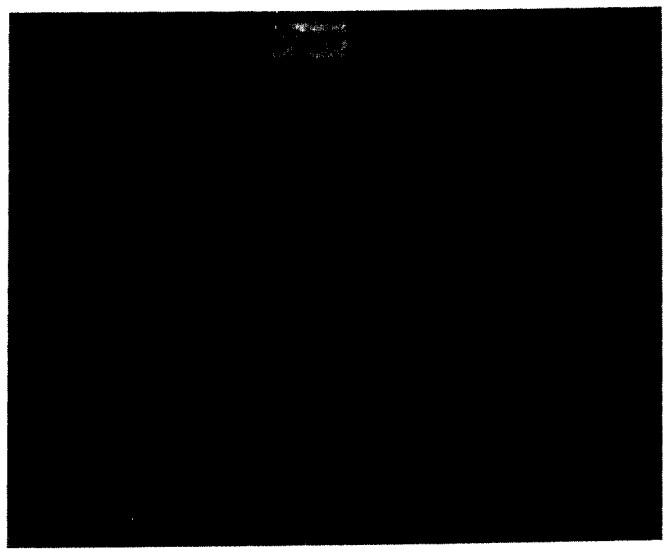
In FIG. 6, using the same materials as in FIG. 5 but in a different ratio (as described below), an even more nearly uniform surface was obtained.

In example 7b, the results of which are shown in FIG. 6, the starting composition of the bath was 50 v/o acetone and 50 v/o diluent. The diluent was 50 w/o polyvinylpyrrolidone-10,000, 50 w/o water and less than ½ w/o isopropyl alcohol. The treated surface is even more nearly uniform than that of Example 7a.

EXAMPLE 8

In this example, instead of an acrylic polymer rod, an acrylonitrile-butadiene-styrene rod was inserted into a bath of which the starting composition was 75 v/o acetone and 25 v/o diluent, where the diluent was 50 w/o PEG-4000 and 50 w/o water. In this example, however, the rate of addition of the diluent and the initial volume were varied from those described above. Here, the rate of addition of diluent was 0.1 ml/min. and the initial volume was 25 ml. However, all other conditions were as described above in Example 4. The resulting surface was very amorphous (i.e., glass-like and showing no structure) with a few flecks scattered throughout the material. The surface looked smooth except for the flecks. Under an optical microscope the surface looked smooth at a magnification of 140×. All machine marks had been obliterated, as viewed at this magnification, and the number of surface imperfections was greatly reduced by the process. SEM's have been obtained for this system. The SEM of the untreated surface showed large and regular furrow-like machining marks at 1000×, whereas the treated sample appeared smooth except for a few (about 10 per 9900 $\mu m^2$) plate-like, raised areas scattered across the surface. The largest of these plates had an area of approximately 65 (μm)² and most of the others were less than ¼ of that size.

EXAMPLE 9

The same basic procedure used in Example 6 was here used, except that the rod was square-shaped, rather than cylindrical, CuCl₂ was here used, and the starting solution was 60 v/o acetone and 40 v/o diluent (made up of 3 parts by weight of water, 3 parts by weight of PEG-4000 and 2 parts by weight of CuCl₂). Again a sharp boundary between the infused sector and the uninfused core was observed and it occurred at about 1/32 inch from the outer surface. This example demonstrates that the sharp boundary is not dependent upon a cylindrical-shaped substrate.

The foregoing description of preferred embodiments of the invention has been presented for purposes of illustration and description. It is not intended to be exhaustive or to limit the invention to the precise forms disclosed, and obviously many modifications and variations are possible in light of the above teaching. The embodiments were chosen and described in order to best explain the principles of the invention and their practical application to thereby enable others skilled in the art to best utilize the invention in various embodiments and with various modifications as are suited to the particular use contemplated. It is intended that the scope of the invention be defined by the claims appended hereto.

What is claimed is:

1. A method of smoothing the surface of an article comprising a first material selected from the group consisting of poly(methyl methacrylate) and acrylonitrile-butadiene-styrene polymers, said method comprising:
    (a) immersing at least a portion of said article into a bath consisting essentially of (1) at least one solvent for said first material and (2) a diluent consisting essentially of at least one nonsolvent for said first material and optional accessory material which is soluble in said bath; and
    (b) slowly removing said solvent from said bath by diluting said bath with said diluent, wherein said nonsolvent is a mixture of water and a water-soluble polymer having a molecular weight within the range from about 2000 to about 20,000, wherein said at least one solvent is selected from the group consisting of ketones and esters which show some significant mutual solubility with water, and wherein the rate of dilution of said bath is such that it results in extraction of said solvent from said first material on a molecular scale, rather than on a massive scale.

2. A method according to claim 1, wherein said first material is poly(methyl methacrylate), wherein said solvent is acetone, and wherein said water-soluble polymer is polyethylene glycol.

3. A method according to claim 1, wherein said polyethylene glycol has a molecular weight within the range from about 3000 to about 6000.

4. A method according to claim 3, wherein the starting composition of said bath is a volume ratio of said solvent:diluent which is within the range from about 40:60 to about 80:20.

5. A method according to claim 4, wherein the weight ratio of water:polyethylene glycol in said nonsolvent is within the range from about 75:25 to about 40:60.

6. A method according to claim 5, wherein said polyethylene glycol has a molecular weight of about 4000, wherein said weight ratio of water:polyethylene glycol in said nonsolvent is about 50:50, and wherein the starting composition of said bath is a volume ratio of said acetone:said diluent which is about 75:25.

7. A method according to claim 1 wherein said water-soluble polymer is polyvinylpyrrolidone (having a molecular weight of about 10,000) and wherein said nonsolvent includes also a small amount of isopropyl alcohol.

8. A method according to claim 7 wherein the starting composition of said bath has a volume ratio of solvent: diluent which is within the range from about 25:75 to about 65:35.

9. A method according to claim 8, wherein the weight ratio of polyvinylpyrrolidone:water is about 50:50 and wherein the starting composition of said bath is a volume ratio of solvent:diluent which is about 50:50.

10. A method according to claim 1 wherein said first material is an acrylonitrile-butadiene-styrene copolymer, wherein said solvent is acetone and wherein said water-soluble polymer is polyethylene glycol.

11. A method according to claim 10, wherein the starting composition of said bath has a volume ratio of solvent:diluent within the range from about 40:60 to about 80:20.

12. A method according to claim 11, wherein the starting composition of said bath has a volume ratio of acetone:diluent of 75:25 and wherein said diluent was 50 weight percent polyethylene glycol-4000 and 50 weight percent water.

* * * * *